(12) United States Patent
Watanabe

(10) Patent No.: US 11,684,322 B2
(45) Date of Patent: Jun. 27, 2023

(54) POSITRON EMISSION TOMOGRAPHY APPARATUS, METHOD, AND STORAGE MEDIUM

(71) Applicant: CANON MEDICAL SYSTEMS CORPORATION, Tochigi (JP)

(72) Inventor: Kanji Watanabe, Nasushiobara (JP)

(73) Assignee: CANON MEDICAL SYSTEMS CORPORATION, Otawara (JP)

(*) Notice: Subject to any disclaimer, the term of this patent is extended or adjusted under 35 U.S.C. 154(b) by 0 days.

(21) Appl. No.: 17/655,894

(22) Filed: Mar. 22, 2022

(65) Prior Publication Data

US 2022/0361827 A1 Nov. 17, 2022

(30) Foreign Application Priority Data

May 13, 2021 (JP) ................................. 2021-081528

(51) Int. Cl.
*A61B 6/03* (2006.01)
*G01T 1/29* (2006.01)
*A61B 6/00* (2006.01)

(52) U.S. Cl.
CPC ............ *A61B 6/037* (2013.01); *A61B 6/4275* (2013.01); *A61B 6/585* (2013.01); *A61B 6/586* (2013.01); *G01T 1/2985* (2013.01)

(58) Field of Classification Search
CPC ....... A61B 6/037; A61B 6/4275; A61B 6/585; A61B 6/586; G01T 1/2985
See application file for complete search history.

(56) References Cited

U.S. PATENT DOCUMENTS 6,799,068 B1 9/2004 Hartmann et al.
2014/0361191 A1* 12/2014 McGowan ............... G01T 1/40
250/336.1

FOREIGN PATENT DOCUMENTS

| JP | 2003-523219 A | 8/2003 |
|---|---|---|
| JP | 2005-106562 A | 4/2005 |
| JP | 2007-147604 A | 6/2007 |

* cited by examiner

*Primary Examiner* — David P Porta
*Assistant Examiner* — Casey Bryant
(74) *Attorney, Agent, or Firm* — Oblon, McClelland, Maier & Neustadt, L.L.P.

(57) ABSTRACT

A positron emission tomography apparatus according to an embodiment includes a plurality of positron emission tomography (PET) detector entities and processing circuitry. The plurality of PET detector entities are arranged in a ring formation. The processing circuitry is configured: to obtain, with respect to each of the plurality of PET detector entities, state information indicating a state of the PET detector entity; to detect an abnormality when an index value indicating a state of any individual or a whole of the plurality of PET detector entities exceeds a threshold value on the basis of the state information; and to detect a state in which the abnormality is not detected on the basis of the state information, but an index value indicating states of at least two of the plurality of PET detector entities is different from an index value indicating states of at least two other PET detector entities.

9 Claims, 5 Drawing Sheets

POSITRON EMISSION TOMOGRAPHY APPARATUS, METHOD, AND STORAGE MEDIUM

CROSS-REFERENCE TO RELATED APPLICATIONS

This application is based upon and claims the benefit of priority from Japanese Patent Application No. 2021-081528, filed on May 13, 2021; the entire contents of which are incorporated herein by reference.

FIELD

Embodiments described herein relate generally to a positron emission tomography apparatus, a method, and a storage medium.

BACKGROUND

Conventionally, Positron Emission Tomography (PET) apparatuses include a PET detector configured to detect gamma rays released as a result of positrons emitted from a tracer administered for an examined subject (hereinafter, "patient") P annihilating with electrons. Generally speaking, those PET apparatuses undergo Quality Check (QC) routinely so as to manage the state of the PET detector.

DETAILED DESCRIPTION

A PET apparatus according to an embodiment includes a plurality of PET detector entities, an obtaining unit, a first detecting unit, and a second detecting unit. The plurality of PET detector entities are arranged in a ring formation. The obtaining unit is configured to obtain, with respect to each of the plurality of PET detector entities, state information indicating a state of the PET detector entity. The first detecting unit is configured to detect an abnormality when an index value indicating a state of any individual or a whole of the plurality of PET detector entities exceeds a threshold value on the basis of the state information. The second detecting unit is configured to detect a state in which the abnormality is not detected on the basis of the state information, but an index value indicating states of at least two of the plurality of PET detector entities is different from an index value indicating states of at least two other PET detector entities.

In the following sections, exemplary embodiments of a PET apparatus will be explained in detail, with reference to the accompanying drawings.

First Embodiment

Figure 1:
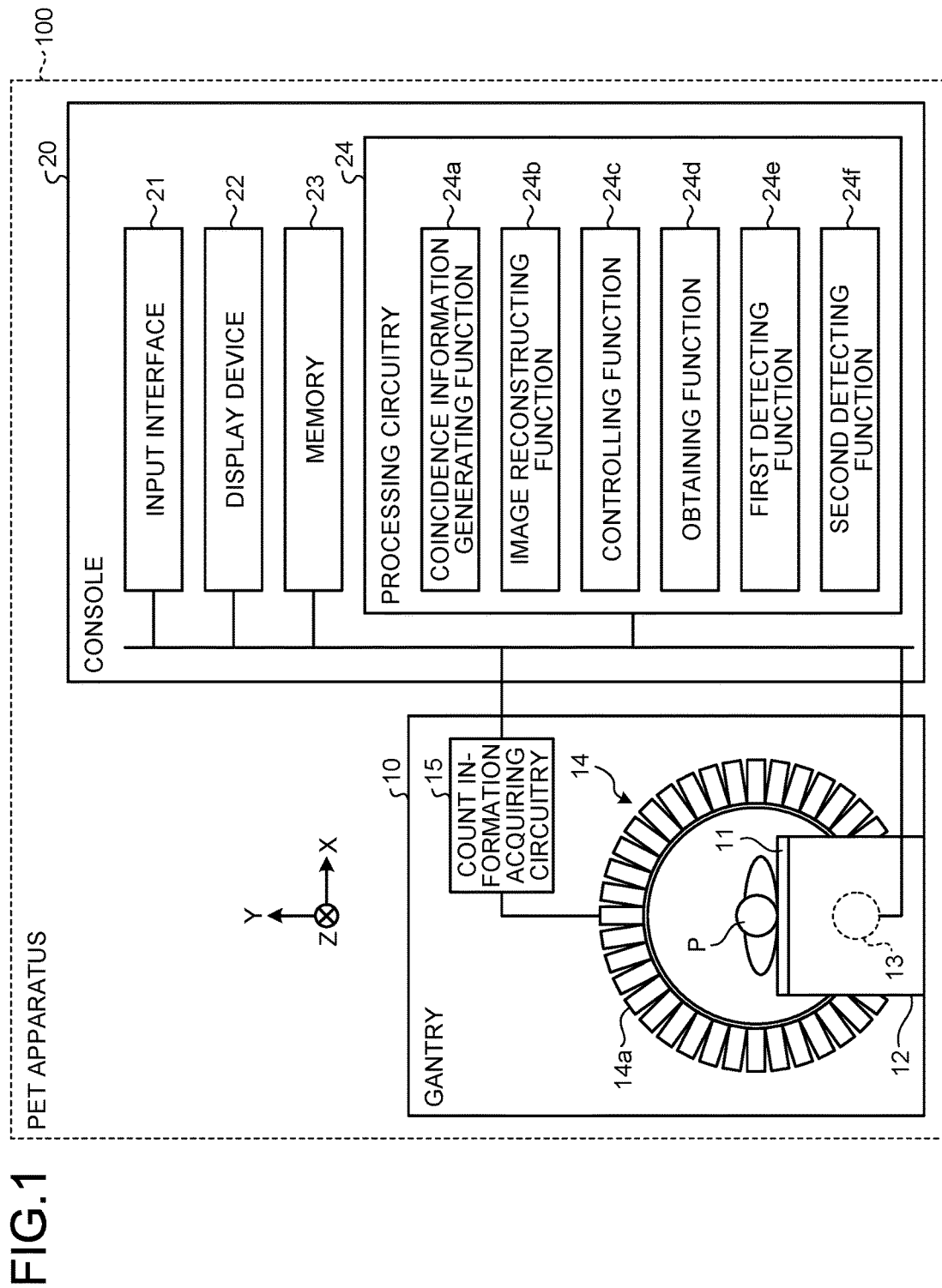
FIG. 1 is a diagram illustrating an exemplary configuration of a PET apparatus according to a first embodiment.

FIG. 1 is a diagram illustrating an exemplary configuration of a PET apparatus according to a first embodiment.

For example, as illustrated in FIG. 1, a PET apparatus 100 according to the present embodiment includes a gantry 10 and a console 20.

The gantry 10 is configured to detect gamma rays released as a result of positrons emitted from a tracer administered for a patient P annihilating with electrons and configured to acquire count information by counting the detected gamma rays. In this situation, the gantry 10 has a circular cylindrical opening part formed so as to horizontally penetrate the gantry 10 and is configured to detect the gamma rays emitted from the patient P placed in the opening part. In the following sections, the direction extending along the axis of the circular cylindrical opening part of the gantry 10 is defined as a Z-axis direction, while the horizontal direction orthogonal to the Z-axis direction is defined as an X-axis direction, and the vertical direction orthogonal to the Z-axis direction is defined as a Y-axis direction.

More specifically, the gantry 10 includes a couchtop 11, a couch 12, a couch driving mechanism 13, a PET detector 14, and count information acquiring circuitry 15.

The couchtop 11 is a bed on which the patient P is placed. For example, the couchtop 11 is formed to have a rectangular flat shape and is arranged so that the longitudinal direction thereof is parallel to the Z-axis direction.

The couch 12 is configured to support the couchtop 11 so as to be movable in the X-axis direction, the Y-axis direction, and the Z-axis direction.

The couch driving mechanism 13 is provided on the inside or the outside of the couch 12 and is configured to move the couchtop 11 supported by the couch 12. For example, when an imaging process is to be performed on the patient P, the couch driving mechanism 13 is configured to move the couchtop 11 on which the patient P is placed, into the opening part of the gantry 10. For example, while the position of the couch 12 is fixed, the couch driving mechanism 13 is configured to move the couchtop 11 over the couch 12. Alternatively, for example, the couch driving mechanism 13 may be configured to move the couch 12 arranged on a movable base, together with the couchtop 11.

The PET detector 14 is configured to detect the gamma rays released as a result of the positrons emitted from the tracer administered for the patient P annihilating with the electrons, to further convert the detected gamma rays into electrical signals, and to output the electrical signals. More specifically, the PET detector 14 includes a plurality of detector units 14a arranged in a ring formation centered on the Z-axis so as to surround the opening part formed in the gantry 10, while the detector units 14a are configured to detect the gamma rays.

The count information acquiring circuitry 15 is configured to acquire the count information by counting the gamma rays on the basis of the electrical signals output from the detector units 14a included in the PET detector 14. More specifically, the count information acquiring circuitry 15 is configured to convert the electrical signals output from the PET detector 14 into digital signals and to generate the count information including detection positions, energy, and detection times of the gamma rays. Further, the count information acquiring circuitry 15 is configured to store the generated count information into a memory 23.

The console 20 is configured to receive various types of operations on the PET apparatus 100 from an operator and to control operational movements of the PET apparatus 100 on the basis of the received operations. More specifically, the console 20 includes an input interface 21, a display device 22, the memory 23, and processing circuitry 24. In this situation, functional units included in the console 20 are connected together via a bus. Although an example has been explained in which the gantry 10 and the console 20 are separate, the gantry 10 may include the console 20 or one or more of the constituent elements of the console 20.

The input interface 21 is configured to receive various types of input operations from the operator, to convert the received input operations into electrical signals, and to output the electrical signals to the processing circuitry 24. For example, the input interface 21 is realized by using a mouse, a keyboard, a trackball, a switch, a button, a joystick, a touchpad on which input operations can be performed by touching an operation surface thereof, a touch screen in which a display screen and a touchpad are integrally formed, a contactless input circuit using an optical sensor, an audio input circuit, and/or the like, which are used for setting an image taking condition, a Region Of Interest (ROI), and the like. Alternatively, for instance, the input interface 21 may be provided for the gantry 10. In an example, the input interface 21 may be configured by using a tablet terminal or the like capable of wirelessly communicating with the main body of the console 20. Further, the input interface 21 does not necessarily have to include physical operation component parts such as a mouse, a keyboard, and/or the like. For instance, possible examples of the input interface 21 include electrical signal processing circuitry configured to receive an electrical signal corresponding to an input operation from an external input device provided separately from the console 20 and to output the electrical signal to the processing circuitry 24.

The display device 22 is configured to display various types of information. For example, the display device 22 is configured to output a PET image generated by the processing circuitry 24, a Graphical User Interface (GUI) used for receiving various types of operations from the operator, and the like. For example, the display device 22 may be a liquid crystal display device or a Cathode Ray Tube (CRT) display device. Alternatively, for instance, the display device 22 may be provided for the gantry 10. Further, for instance, the display device 22 may be of a desktop type or may be configured by using a tablet terminal or the like capable of wirelessly communicating with the main body of the console 20.

The memory 23 is configured to store therein various types of data used in the PET apparatus 100. For example, the memory 23 is realized by using a semiconductor memory element such as a Random Access Memory (RAM) or a flash memory or a hard disk, an optical disk, or the like.

The processing circuitry 24 is configured to control operational movements of the entirety of the PET apparatus 100. More specifically, the processing circuitry 24 includes a coincidence information generating function 24a, an image reconstructing function 24b, a controlling function 24c, an obtaining function 24d, a first detecting function 24e, and a second detecting function 24f.

The coincidence information generating function 24a is configured to generate coincidence information by using the count information acquired by the count information acquiring circuitry 15. More specifically, the coincidence information generating function 24a is configured to refer to the count information stored in the memory 23 and to search for sets each made up of pieces of count information in which annihilated gamma rays were counted substantially at the same time, on the basis of the detection times in pieces of count information. After that, the coincidence information generating function 24a is configured to generate the coincidence information in which the sets of count information found in the search are kept in correspondence and to store the generated coincidence information into the memory 23.

The image reconstructing function 24b is configured to reconstruct a PET image on the basis of the coincidence information generated by the coincidence information generating function 24a. More specifically, the image reconstructing function 24b is configured to reconstruct the PET image by reading the coincidence information stored in the memory 23 and performing a backprojection process while using the read coincidence information as projection data. Further, the image reconstructing function 24b is configured to store the reconstructed PET image into the memory 23.

The controlling function 24c is configured to control the entirety of the PET apparatus 100 by controlling functional units of the gantry 10 and the console 20. For example, the controlling function 24c is configured to move the couchtop 11 by controlling the couch driving mechanism 13. As another example, the controlling function 24c is configured to acquire the count information of the annihilated gamma rays emitted from the patient P by controlling the count information acquiring circuitry 15.

Further, the obtaining function 24d, the first detecting function 24e, and the second detecting function 24f will be explained in detail later.

For example, the processing circuitry 24 is realized by using a processor. In that situation, the processing functions included in the processing circuitry 24 are stored in the memory 23 in the form of computer-executable programs. Further, the processing circuitry 24 is configured to realize the processing functions corresponding to the programs, by reading and executing the programs from the memory 23. In other words, the processing circuitry 24 that has read the programs has the processing functions illustrated within the processing circuitry 24 in FIG. 1.

The exemplary configuration of the PET apparatus 100 according to the first embodiment has thus been explained. In this situation, in the PET apparatus 100 according to the present embodiment, as explained above, the PET detector 14 includes the plurality of detector units 14a arranged in the ring formation.

Generally speaking, the PET apparatus 100 structured as described above undergoes a QC process routinely, so as to manage the state of the PET detector 14.

Usually, during a QC process, with respect to each of the plurality of detector units 14a included in the PET detector 14, a parameter value indicating the state of the detector unit 14a is obtained, so as to evaluate the state of the PET detector 14 on the basis of the parameter values of the individual detector units 14a and an average value of the parameter values of all the detector units 14a. In this situation, the parameter values indicating the states of the detector units 14a may be those of, for example, temperature, energy, time information, or the like.

However, for the QC process, because specification values are provided for the parameter values of the individual detector units 14a and for the average value of the parameter values of all the detector units 14a, there are some situations where it is not possible to properly manage the state of the PET detector 14.

Figure 2:
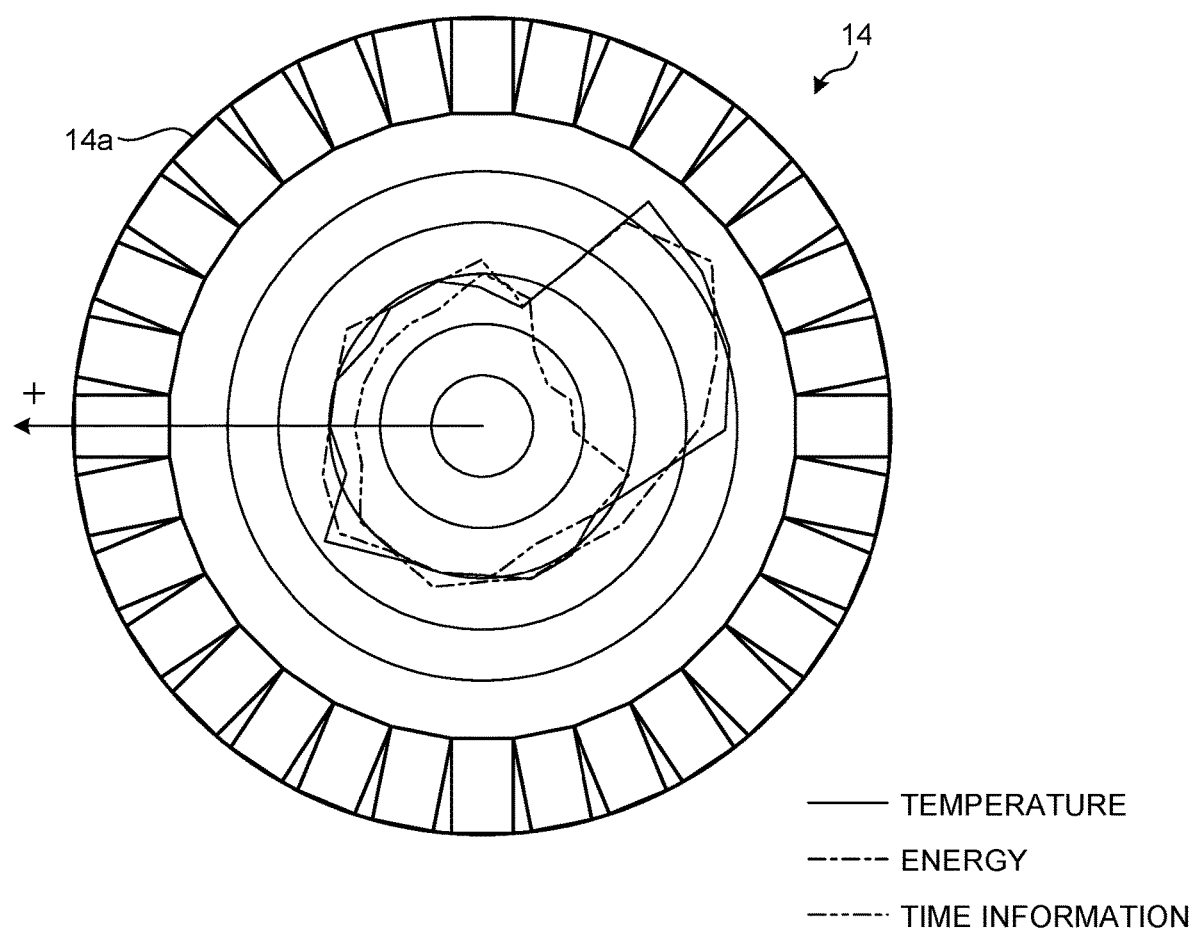
FIG. 2 is a drawing illustrating an example of a state indicating respective parameter values of a plurality of detector units included in a PET detector according to the first embodiment.

FIG. 2 is a drawing illustrating an example of a state indicating respective parameter values of the plurality of detector units 14a included in the PET detector 14 according to the first embodiment.

For example, as illustrated in FIG. 2, in the PET detector 14, due to deterioration over time, failures, or the like of the individual detector units 14a, the parameter values indicating temperatures, energy levels, or time information may become unequal among the plurality of detector units 14a, or there may be a difference in the parameter values between opposing detector units 14a.

When the parameter values are unequal among the plurality of detector units 14a or when there is a difference in the parameter values between opposing detector units 14a as described herein, it is necessary to calibrate the PET detector 14 because there is a possibility that image quality may be affected. In this situation, the calibration denotes correcting the parameter values of the detector units 14a included in the PET detector 14 so as to be appropriate values.

However, for the QC process described above, because the specification values are provided for the parameter values of the individual detector units 14a and for the average value of the parameter values of all the detector units 14a, there is a possibility that, even when the PET detector 14 is in the state where images can be affected, the detector units 14a individually or as a whole may inadvertently fall in a specification range set by the QC process. For this reason, the abovementioned QC process may not be able to properly manage the state of the PET detector 14 in some situations.

In view of the circumstances described above, the PET apparatus 100 according to the present embodiment is configured so as to be able to properly manage the state of the PET detector 14.

More specifically, the obtaining function 24d of the processing circuitry 24 is configured to obtain, with respect to each of the plurality of detector units 14a, a parameter value indicating the state of the detector unit 14a. In this situation, the obtaining function 24d is an example of the obtaining unit. Further, the detector units 14a are examples of the PET detector entities. The parameter values form an example of the state information.

Further, on the basis of the parameter values obtained by the obtaining function 24d, the first detecting function 24e of the processing circuitry 24 is configured to detect an abnormality when an index value indicating the state of any individual or the whole of the plurality of detector units 14a exceeds a threshold value. In this situation, the first detecting function 24e is an example of the first detecting unit.

Further, on the basis of the parameter values obtained by the obtaining function 24d, the second detecting function 24f of the processing circuitry 24 is configured to detect a state in which no abnormality is detected by the first detecting function 24e, but an index value indicating the states of at least two of the plurality of detector units 14a is different from an index value indicating the states of at least two other detector units 14a. In this situation, the second detecting function 24f is an example of the second detecting unit.

With this configuration, even when no abnormality is detected from the index values indicating the states of the individuals or the whole of the plurality of detector units 14a, it is possible to detect a state in which the index values are unequal among the plurality of detector units 14a or a state in which there is a large difference between certain index values. Consequently, according to the present embodiment, it is possible to properly manage the state of the PET detector 14.

Next, the obtaining function 24d, the first detecting function 24e, and the second detecting function 24f presented above will be explained in detail.

To begin with, while the PET apparatus 100 is in operation, the obtaining function 24d is configured to occasionally obtain the parameter values indicating the states of the detector units 14a. Further, the obtaining function 24d is configured to store the obtained parameter values into the memory 23 in correspondence with the points in time of acquisition.

For example, as the parameter values, the obtaining function 24d obtains at least one selected from among temperatures, energy levels, and time information. In this situation, the energy levels denote, for example, energy resolutions, energy peak values, or the like. The time information denotes, for example, temporal resolutions, delay periods, or the like. The temporal resolutions indicate a variation in differences in the detection times among opposing detector units. The delay periods indicate staggered amounts between opposing detector units, with respect to times at which an energy peak value is detected.

Subsequently, when the QC process is carried out, the first detecting function 24e is configured to detect abnormalities of the PET detector 14 on the basis of the parameter values of the detector units 14a obtained by the obtaining function 24d, in response to an instruction from a user or the like.

More specifically, the first detecting function 24e is configured to refer to the parameter values of the detector units 14a stored in the memory 23 and to detect an abnormality, when the parameter value of any of the plurality of detector units 14a exceeds a first threshold value or when an average value of the parameter values of all the detector units 14a exceeds a second threshold value. In this situation, the first threshold value and the second threshold value are set according to the specification values for the QC process. Further, the first threshold value may be equal to or may be different from the second threshold value. Further, upon detection of the abnormality, the first detecting function 24e is configured to issue a notification through the display device 22 or the like to indicate that the PET detector 14 needs to be calibrated.

After that, while the PET apparatus 100 is in operation, the second detecting function 24f is configured to detect the state of the PET detector 14, by occasionally analyzing the parameter values of the detector units 14a obtained by the obtaining function 24d.

In the present embodiment, the second detecting function 24f is configured to detect a state in which the index value indicating the states of at least two of the plurality of detector units 14a is different from the index value indicating the states of at least two detector units 14a other than the at least two detector units 14a.

In this situation, for example, the at least two detector units 14a are either at least two detector units 14a arranged adjacent to each other or two detector units 14a arranged opposite to each other. Further, the index values are either the parameter values themselves indicating the states of the detector units 14a or values calculated from the parameter values.

More specifically, the second detecting function 24f is configured to refer to the parameter values of the detector units 14a stored in the memory 23 and to calculate, with respect to each set made up of at least two detector units 14a, the index value indicating the states of the detector units 14a. Further, the second detecting function 24f is configured to detect the state in which the index value of one of the sets is different from the index values of the other sets.

For example, the second detecting function 24f is configured to detect the state in which the index values of the sets each made up of at least two detector units 14a are different, on the basis of a threshold value smaller than the threshold value used by the first detecting function 24e.

Figure 3:
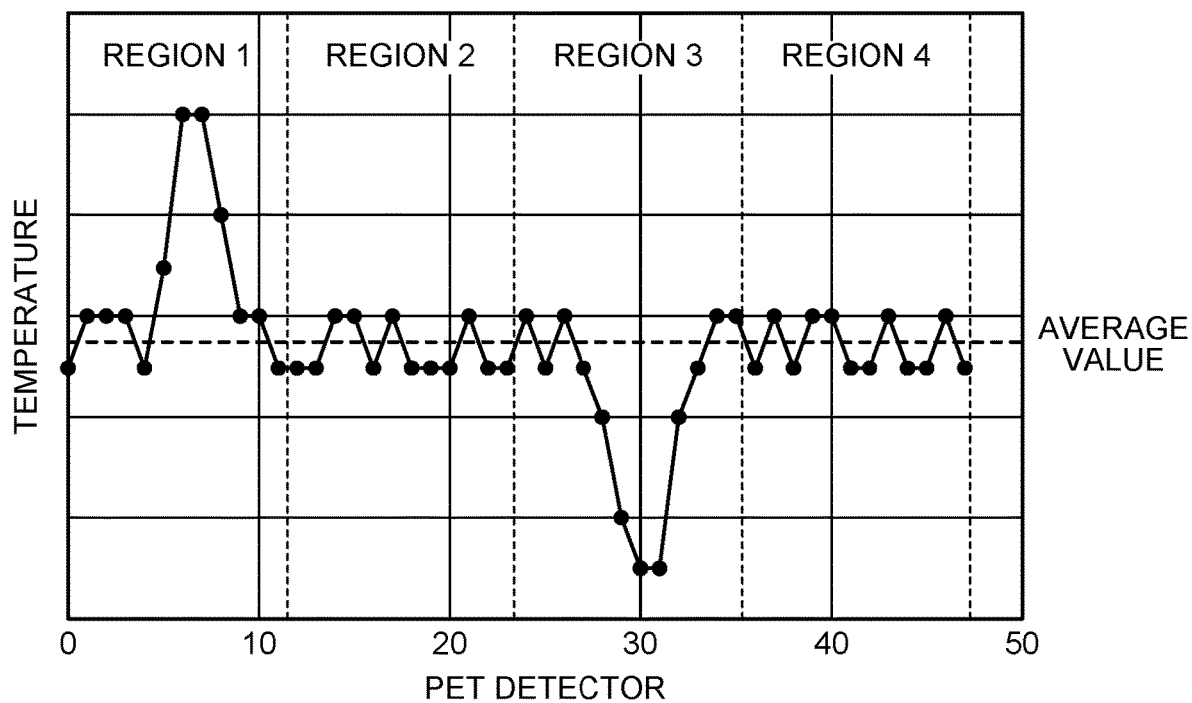
FIG. 3 is a chart illustrating an example of a process of detecting a state of a PET detector 14 performed by a second detecting function according to the first embodiment.

FIG. 3 is a chart illustrating an example of a process of detecting the state of the PET detector 14 performed by the second detecting function 24f according to the first embodiment. In FIG. 3, the horizontal axis indicates numbers identifying the plurality of detector units 14a included in the PET detector 14, whereas the vertical axis expresses temperatures of the detector units 14a.

For example, as illustrated in FIG. 3, let us assume that, in a hardware configuration, the detector units 14a included in the PET detector 14 are separated into a plurality of regions, in groups of a predetermined number of detector units 14a positioned adjacent to each other.

In this situation, for example, the second detecting function 24f is configured to calculate an average temperature value of the detector units 14a, with respect to each of the regions. Further, when the average value of any of the regions exceeds a threshold value, the second detecting function 24f is configured to determine that the temperatures of the detector units 14a in the region are different from the temperatures of the detector units 14a in the other regions.

In the present example, the parameter values are of the temperatures. However, the parameter values used by the second detecting function 24f may be of energy levels, time information, or the like.

Further, possible processes of detecting the state of the PET detector 14 performed by the second detecting function 24f are not limited to the example described above.

For instance, the second detecting function 24f may be configured to determine that index values are different, when an index value indicating the states of at least two of the plurality of detector units 14a is different, by a value equal to or larger than a predetermined value, from an index value indicating the states of at least two detector units 14a other than the at least two detector units 14a.

In yet another example, the second detecting function 24f may identify the largest value and the smallest value among the average values of the parameter values each calculated for a different one of the regions of the detector units 14a, so as to calculate the difference between the identified largest and smallest values. Further, the second detecting function 24f compares the calculated difference with the average values of the parameter values of all the detector units 14a and, when any of the ratios thereof or the gaps therebetween exceeds a threshold value, determines that the index value of the detector units 14a in a certain region is different from index values of the detector units 14a in the other regions.

After the state of the PET detector 14 is detected in this manner, the second detecting function 24f is configured to determine whether or not the PET detector 14 needs to be calibrated, in accordance with the detected state of the PET detector 14.

More specifically, the second detecting function 24f is configured to determine that the calibration is necessary when having detected the state in which the index value indicating the states of at least two of the plurality of detector units 14a included in the PET detector 14 is different from the index value indicating the states of at least two detector units 14a other than the at least two detector units 14a. Otherwise, it is determined that the calibration is not necessary.

Further, when having determined that the PET detector 14 needs to be calibrated, the second detecting function 24f is configured to issue a notification with a proposal for the calibration, on the display device 22 or the like. In contrast, when having determined that the PET detector 14 does not need to be calibrated, the second detecting function 24f is configured to allow the apparatus to keep being used without issuing the notification with the proposal for the calibration.

With the configuration described above, when the states of two or more of the detector units 14a in a positional relationship (e.g., being positioned adjacent to each other or opposite to each other) that can impact the image quality have changed, it is possible to calibrate the PET detector 14, so that the calibration prevents capabilities of the PET apparatus 100 from being degraded.

Figure 4:
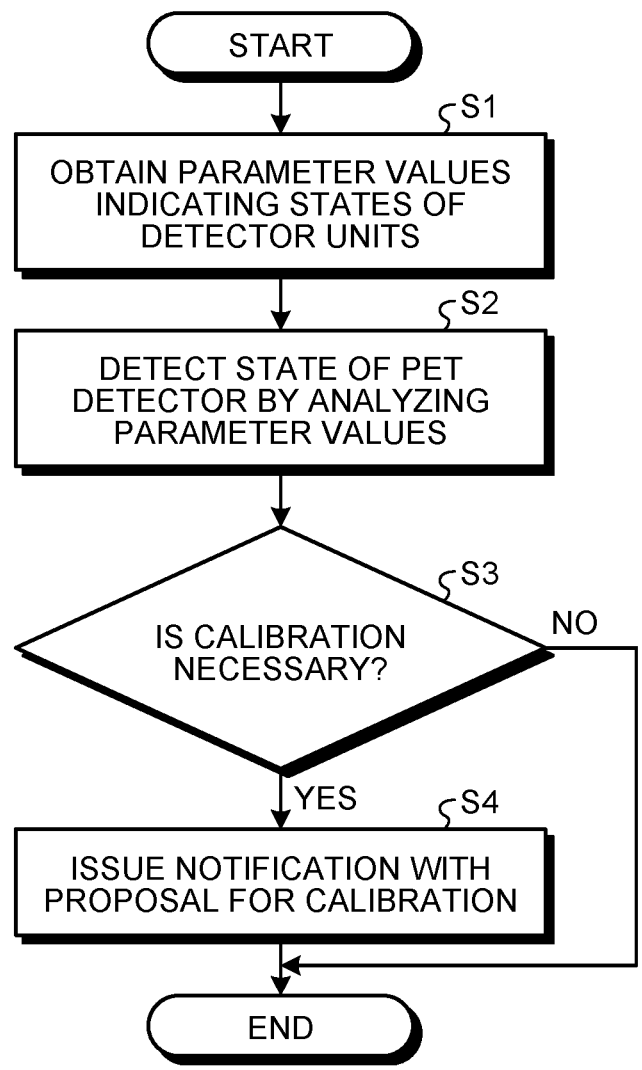
FIG. 4 is a flowchart illustrating a processing procedure in a process performed by an obtaining function and the second detecting function according to the first embodiment.

FIG. 4 is a flowchart illustrating a processing procedure in a process performed by the obtaining function 24d and the second detecting function 24f according to the first embodiment.

In the present embodiment, the abnormality detecting process by the first detecting function 24e is carried out when the QC process is performed. In contrast, the process of detecting the state of the PET detector 14 performed by the second detecting function 24f is occasionally carried out while the PET apparatus 100 is in operation, as described below.

For example, as illustrated in FIG. 4, the obtaining function 24d occasionally obtains the parameter values indicating the states of the detector units 14a while the PET apparatus 100 is in operation (step S1).

Further, while the PET apparatus 100 is in operation, the second detecting function 24f detects the state of the PET detector 14, by occasionally analyzing the parameter values of the detector units 14a obtained by the obtaining function 24d (step S2).

Subsequently, in accordance with the detected state of the PET detector 14, the second detecting function 24f determines whether or not the PET detector 14 needs to be calibrated (step S3).

Further, when having determined that the PET detector 14 needs to be calibrated (step S3: Yes), the second detecting function 24f issues a notification with a proposal for the calibration on the display device 22 or the like (step S4).

On the contrary, when having determined that the PET detector 14 does not need to be calibrated (step S3: No), the second detecting function 24f allows the apparatus to keep being used, without issuing the notification with the proposal for the calibration.

The obtaining function 24d, the first detecting function 24e, and the second detecting function 24f included in the processing circuitry 24 have thus been explained. As mentioned earlier, when the processing circuitry 24 is realized by one or more processors, the processes performed by the obtaining function 24d, the first detecting function 24e, and the second detecting function 24f are realized, for example, as a result of the processing circuitry 24 reading and executing the programs corresponding to the processing functions from the memory 23.

As explained above, in the first embodiment, with respect to each of the plurality of detector units 14a, the obtaining function 24d is configured to obtain the state information of the detector unit 14a. Further, on the basis of the state information obtained by the obtaining function 24d, the first detecting function 24e is configured to detect an abnormality, when the index value indicating the states of any individual or the whole of the plurality of detector units 14a exceeds the threshold value. Further, the second detecting function 24f is configured to detect the state in which no abnormality is detected by the first detecting function 24e on the basis of the state information obtained by the obtaining function 24d, but the index value indicating the states of at least two of the plurality of detector units 14a is different from the index value indicating the states of at least two other detector units 14a.

With this configuration, even when no abnormality is detected from the index values indicating the individuals or the whole of the plurality of detector units 14a, it is possible to detect a state in which the index values are unequal among the plurality of detector units 14a or a state in which there is a large difference between certain index values, by comparing the index values of the sets each made up of at least two detector units 14a. Consequently, according to the present embodiment, it is possible to properly manage the state of the PET detector 14.

Further, in the first embodiment, when the parameter values of the detector units 14a have a tendency among the plurality of detector units 14a although the specifications set for the QC process are satisfied, it is possible to prevent image quality from being deteriorated by proposing the calibration. As a result, it is possible to reduce burdens in the managing of the apparatus.

The first embodiment has thus been explained. A part of the configuration of the PET apparatus 100 described above may be carried out with a modification as appropriate. Thus, modification examples of the first embodiment will be explained below as other embodiments. In the following embodiments, differences from the first embodiment will primarily be explained. Explanations of some of the features that are the same as those already explained will be omitted.

Second Embodiment

For instance, in the first embodiment above, the example was explained in which the state of the PET detector 14 is detected on the basis of one type of parameter values; however, possible embodiments are not limited to this example.

For instance, the state of the PET detector 14 may be detected on the basis of a plurality of types of parameter values. In the following sections, this example will be explained as a second embodiment.

In the present embodiment, the obtaining function 24d is configured to obtain, as parameter values indicating the states of the detector units 14a, first parameter values and second parameter values that are of a different type from the first parameter values. In this situation, the obtaining function 24d is an example of the obtaining unit. Further, the first parameter values form an example of the first state information. The second parameter values form an example of the second state information.

Further, with respect to every two or more of the detector units 14a, the second detecting function 24f is configured to calculate, as the index values, a first index value from the first parameter value and a second index value from the second parameter value, so as to detect a state in which the index values are different on the basis of differences among the first parameter values and among the second parameter values.

Figure 5:
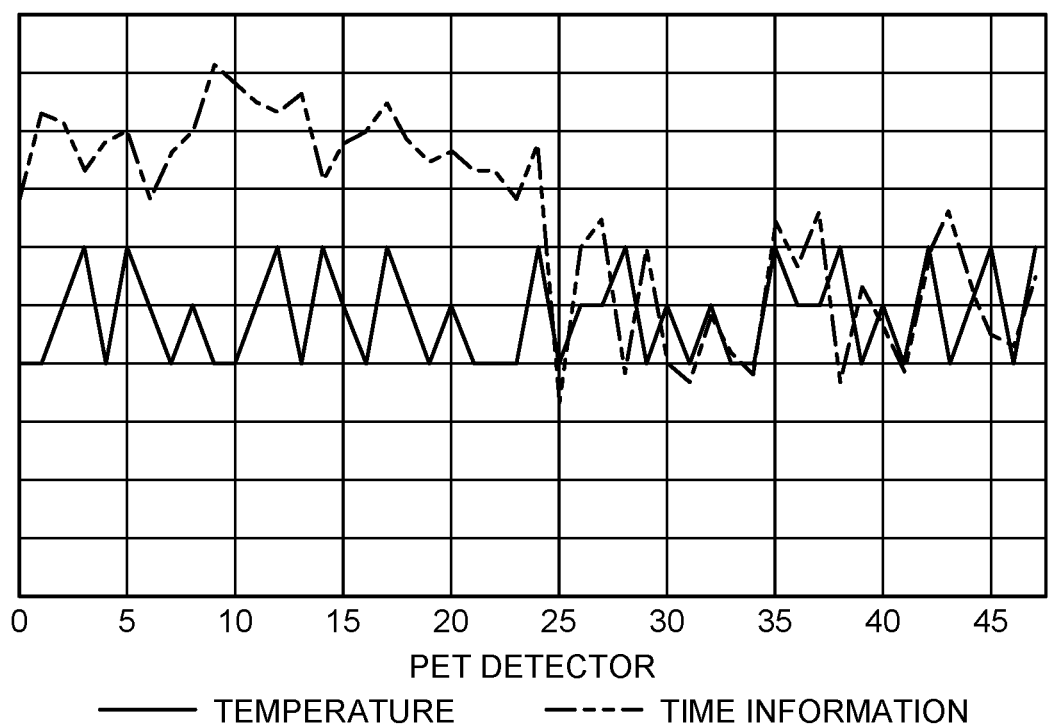
FIG. 5 is a chart illustrating an example of a process of detecting a state of a PET detector performed by a second detecting function according to a second embodiment.

FIG. 5 is a chart illustrating an example of a process of detecting a state of the PET detector 14 performed by the second detecting function 24f according to the second embodiment. In FIG. 5, the horizontal axis indicates numbers identifying the plurality of detector units 14a included in the PET detector 14, whereas the vertical axis expresses temperatures and time information of the detector units 14a.

For example, as illustrated in FIG. 5, among the plurality of detector units 14a, there is a possibility in some situations that a tendency of the time information of the detector may change independently of a tendency of the temperatures so that, as a result, there may be a large difference between the largest value and an average value of the time information.

In those situations, for example, the second detecting function 24f is configured to determine that pieces of time information are different, when the gap between the pieces of time information is equal to or larger than a time information conversion value calculated from a temperature difference, between at least two of the plurality of detector units 14a and at least two detector units 14a other than the at least two detector units 14a. In this situation, for example, the second detecting function 24f is configured to calculate the time information conversion value as "the temperature difference×5 [ps/° C.]".

Further, for example, upon detection of the state in which the pieces of time information are different, the second detecting function 24f is configured to issue a notification with a proposal for calibration, on the display device 22 or the like, so that only the time information is to be calibrated.

With this configuration, even when no abnormality is detected from the index values indicating the individuals or the whole of the plurality of detector units 14a, it is possible to detect a state in which the index values are unequal among the plurality of detector units 14a or a state in which there is a large difference between certain index values, on the basis of the difference in tendencies between the plurality of index values. Consequently, according to the second embodiment also, it is possible to properly manage the state of the PET detector 14.

Third Embodiment

Further, for instance, in the first embodiment above, the example was explained in which the state is detected in which the index values at the same point in time are different between at least two detector units 14a and at least two other detector units 14a; however, possible embodiments are not limited to this example. For instance, it is also acceptable to detect a state in which index values are different between different points in time, with respect to at least two detector units 14a. In the following sections, this example will be explained as a third embodiment.

In the present embodiment, the second detecting function 24f may detect a state in which an index value indicating states of at least two of the plurality of detector units 14a is different from an index value indicating states of the at least two detector units 14a at an earlier point in time.

More specifically, the second detecting function 24f is configured to refer to the parameter values of the detector units 14a stored in the memory 23 so as to calculate, with respect to each of the sets made up of at least two detector units 14a, a most recent index value from the most recently obtained parameter values, and to further calculate a past index value from parameter values obtained earlier than the most recent time. For example, the second detecting function 24f may be configured to calculate the past index value from the parameter values at the point in time when the QC process was previously performed.

After that, with respect to each of the sets of the detector units 14a, the second detecting function 24f is configured to detect a state in which the most recent index value is different from the past index value. In this situation, for example, the second detecting function 24f is configured to determine that the index values are different when the most recent index value is different from the past index value by a value equal to or larger than a predetermined value.

With this configuration, even when no abnormality is detected from the index values indicating the individuals or the whole of the plurality of detector units 14a, it is possible to detect a state in which the index values are unequal among the plurality of detector units 14a or a state in which there is a large difference between certain index values, by making the comparison with the past point in time. Consequently, according to the third embodiment also, it is possible to properly manage the state of the PET detector 14.

Further, in the third embodiment, among the plurality of detector units 14a, when the states of the detector units 14a are predicted to become worse due to chronological changes although the specifications set for the QC process are satisfied, it is possible to prevent image quality from being deteriorated by proposing the calibration. As a result, it is possible to reduce burdens in the managing of the apparatus.

Other Embodiments

In the embodiments described above, the example was explained in which the state is detected with respect to each of the detector units 14a; however, possible embodiments are not limited to this example. For instance, when the detector units 14a included in the PET detector 14 are structured as a plurality of detector modules 14b arranged in the Z-axis direction, a state may be detected with respect to each of the detector modules 14b. In that situation, the detector modules 14b are examples of the PET detector entities.

Further, in the embodiments described above, the example was explained in which the obtaining unit, the first detecting unit, and the second detecting unit of the present disclosure are realized by the obtaining function 24d, the first detecting function 24e, and the second detecting function 24f of the processing circuitry 24; however, possible embodiments are not limited to this example. For instance, instead of being realized by the obtaining function 24d, the first detecting function 24e, and the second detecting function 24f as described in the embodiments, the functions of the obtaining unit, the first detecting unit, and the second detecting unit of the present disclosure may be realized by hardware alone, software alone, or a combination of hardware and software.

Further, in the embodiments described above, the processing circuitry does not necessarily have to be realized by a single processor and may be structured by combining together a plurality of independent processors, so that the processing functions are realized as a result of the processors executing the programs. Further, the processing functions of the processing circuitry may be realized as being distributed among or integrated into one or more pieces of processing circuitry as appropriate. Furthermore, the processing functions of the processing circuitry may be realized by a combination of hardware such as circuitry and software. In addition, although the example was explained in the above sections in which the programs corresponding to the processing functions are stored in the single memory, possible embodiments are not limited to this example. For instance, it is acceptable to store the programs corresponding to the processing functions in a plurality of memories in a distributed manner, so that the processing circuitry reads and executes the programs from the memories.

Further, the term "processor" used in the above explanations of the embodiments denotes, for example, a Central Processing Unit (CPU), a Graphics Processing Unit (GPU), or a circuit such as an Application Specific Integrated Circuit (ASIC) or a programmable logic device (e.g., a Simple Programmable Logic Device [SPLD], a Complex Programmable Logic Device [CPLD], or a Field Programmable Gate Array [FPGA]). In this situation, instead of having the programs saved in the memory, it is also acceptable to directly incorporate the programs in the circuitry of one or more processors. In that situation, the one or more processors realize the functions by reading and executing the programs incorporated in the circuitry thereof. Further, the processors of the present embodiments do not each necessarily have to be structured as a single circuit. It is also acceptable to structure one processor by combining together a plurality of independent circuits, so as to realize the functions thereof.

In the present example, the programs executed by the processors are provided as being incorporated, in advance, in a Read Only Memory (ROM), or the like. The programs may be provided as being recorded in a non-transitory computer-readable storage medium such as a Compact Disk Read-Only Memory (CD-ROM), a Flexible Disk (FD), a Compact Disk Recordable (CD-R), a Digital Versatile Disk (DVD), or the like, in a file in a format that is installable or executable by these devices. Further, the programs may be stored in a computer connected to a network such as the Internet so as to be provided or distributed as being downloaded via the network. For example, the programs are structured with modules including the processing functions described above. In the actual hardware, as a result of a CPU reading and executing the programs from a storage medium such as a ROM, the modules are loaded into a main storage device and generated in the main storage device.

Further, in the above embodiments, the constituent elements of the apparatuses and devices in the drawings are based on functional concepts. Thus, it is not necessarily required to physically configure the constituent elements as indicated in the drawings. In other words, specific modes of distribution and integration of the apparatuses and devices are not limited to those illustrated in the drawings. It is acceptable to functionally or physically distribute or integrate all or a part of the apparatuses and devices in any arbitrary units, depending on various loads and the status of use. Further, all or an arbitrary part of the processing functions implemented by the apparatuses and devices may be realized by a CPU and a program analyzed and executed by the CPU or may be realized as hardware using wired logic.

In addition, with regard to the processes explained in the above embodiments, it is acceptable to manually perform all or a part of the processes described as being performed automatically. Conversely, by using a publicly-known method, it is also acceptable to automatically perform all or a part of the processes described as being performed manually. Further, unless noted otherwise, it is acceptable to arbitrarily modify any of the processing procedures, the controlling procedures, specific names, and various information including various types of data and parameters that are presented in the above text and the drawings.

According to at least one aspect of the embodiments described above, it is possible to properly manage the state of the PET detector.

While certain embodiments have been described, these embodiments have been presented by way of example only, and are not intended to limit the scope of the inventions.

Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A positron emission tomography apparatus comprising:
a plurality of Positron Emission Tomography (PET) detector entities arranged in a ring formation; and
processing circuitry configured
to obtain, with respect to each of the plurality of PET detector entities, state information indicating a state of the PET detector entity,
to detect an abnormality when an index value indicating a state of any individual or a whole of the plurality of PET detector entities exceeds a first threshold value on a basis of the state information, and
to detect a state in which the abnormality is not detected on the basis of the state information, but an index value indicating states of at least two of the plurality of PET detector entities is different from an index value indicating states of at least two other PET detector entities.

2. The positron emission tomography apparatus according to claim 1, wherein the processing circuitry detects the state in which the index values are different, on a basis of a second threshold value smaller than the first threshold value.

3. The positron emission tomography apparatus according to claim 1, wherein the processing circuitry detects the state in which the index value indicating the states of at least two of the plurality of PET detector entities is different from the index value indicating the states of at least two PET detector entities other than the at least two PET detector entities.

4. The positron emission tomography apparatus according to claim 1, wherein the processing circuitry detects a state in which an index value indicating states of at least two of the plurality of PET detector entities is different from an index value indicating states of the at least two PET detector entities at an earlier point in time.

5. The positron emission tomography apparatus according to claim 1, wherein the at least two PET detector entities are at least two PET detector entities positioned adjacent to each other or two PET detector entities arranged opposite to each other.

6. The positron emission tomography apparatus according to claim 1, wherein the processing circuitry is configured to obtain, as the state information, first state information and second state information that is of a different type from the first state information, and the processing circuitry is configured to calculate, with respect to every two or more of the PET detector entities, a first index value from the first state information and a second index value from the second state information as the index values and is configured to detect the state in which the index values are different, on the basis of differences among the first index values and among the second index values.

7. The positron emission tomography apparatus according to claim 1, wherein the processing circuitry is configured, upon detection of the state in which the index values are different, to issue a notification with information proposing that the PET detector entities be calibrated.

8. A method to be applied to a positron emission tomography apparatus including a plurality of Positron Emission Tomography (PET) detector entities arranged in a ring formation, the method comprising:
obtaining, with respect to each of the plurality of PET detector entities, state information indicating a state of the PET detector entity;
detecting an abnormality when an index value indicating a state of any individual or a whole of the plurality of PET detector entities exceeds a threshold value on a basis of the state information; and
detecting a state in which the abnormality is not detected on the basis of the state information, but an index value indicating states of at least two of the plurality of PET detector entities is different from an index value indicating states of at least two other PET detector entities.

9. A non-transitory computer-readable storage medium having recorded therein a plurality of computer-executable instructions that are applied to a positron emission tomography apparatus including a plurality of Positron Emission Tomography (PET) detector entities arranged in a ring formation and that cause a computer to execute:
obtaining, with respect to each of the plurality of PET detector entities, state information indicating a state of the PET detector entity;
detecting an abnormality when an index value indicating a state of any individual or a whole of the plurality of PET detector entities exceeds a threshold value on a basis of the state information; and
detecting a state in which the abnormality is not detected on the basis of the state information, but an index value indicating states of at least two of the plurality of PET detector entities is different from an index value indicating states of at least two other PET detector entities.

* * * * *